US00PP16970P2

(12) United States Plant Patent
de Groot

(10) Patent No.: US PP16,970 P2
(45) Date of Patent: Aug. 8, 2006

(54) ***ROSA* PLANT NAMED 'RUIZ012A'**

(50) Latin Name: *Rosa*
Varietal Denomination: RUIZ012A

(75) Inventor: Henk C. A. de Groot, De Kwakel (NL)

(73) Assignee: De Ruiter's Nieuwe Rozen B.V., De Kwakel (NL)

( * ) Notice: Subject to any disclaimer, the term of this patent is extended or adjusted under 35 U.S.C. 154(b) by 400 days.

(21) Appl. No.: 10/894,197

(22) Filed: Jul. 19, 2004

(51) Int. Cl.
*A01H 5/00* (2006.01)

(52) U.S. Cl. ..... Plt./122
(58) Field of Classification Search ..... Plt./122, Plt./129
See application file for complete search history.

*Primary Examiner*—Anne Marie Grunberg
*Assistant Examiner*—June Hwu
(74) *Attorney, Agent, or Firm*—Mark P. Bourgeois

(57) ABSTRACT

A new cultivar of *Rosa* plant named 'RUIZ012A' that is characterized by a compact habit, long life and red flowers.

1 Drawing Sheet

Botanical classification: *Rosa.*
Variety denomination: 'RUIZ012A'.

BACKGROUND OF THE INVENTION

The present invention relates to a new and distinct cultivar of Rose plant botanically known as *Rosa* and hereinafter referred to by the cultivar name 'RUIZ012A'.

The new cultivar is the product of a breeding program conducted by the inventor in a cultivated area of Hazerswoude, The Netherlands. The objective of the breeding program was to develop miniature roses with attractive flower and foliage colors. 'RUIZ012A' is a hybrid that originated from the induced hybridization of the female or seed parent *Rosa* 'Ruiscar' (not patented) and the male or pollen parent *Rosa* 'Poulracos' (not patented). The cultivar 'RUIZ012A' was selected by the inventor in May of 2000 as a single plant within the progeny of the stated cross in a controlled environment of Hazerswoude, The Netherlands.

The closest comparison plant is *Rosa* 'Ruiskjol' (U.S. Plant Pat. No. 12,672) 'RUIZ012A' is distinguishable from 'Ruiskjol' by larger lighter color flowers, leaves with a dark green upper side and a grey-green under side and a more compact habit.

The new cultivar 'RUIZ012A' is distinguishable from the female parent *Rosa* 'Ruiscar' in having dark red flowers. The flowers of 'Ruiscar' are pink with a yellow center. The new cultivar 'RUIZ012A' is distinguishable from the male parent *Rosa* 'Poulracos' in having larger flowers.

Asexual reproduction by cuttings of the new cultivar 'RUIZ012A' was first performed in December of 2000 in Hazerwsoude, The Netherlands. Since that time, under careful observation, the unique characteristics of the new Rose cultivar have been uniform, stable and reproduced true to type in successive generations of asexual reproduction.

SUMMARY OF THE INVENTION

The following represent the distinguishing characteristics of the new *Rosa* cultivar 'RUIZ012A'. These traits in combination distinguish 'RUIZ012A' as a new and distinct cultivar apart from all other existing varieties of *Rosa* known to the inventor. 'RUIZ012A' has not been tested under all possible conditions and phenotypic differences may be observed with variations in environmental, climatic, and cultural conditions, however, without any variance in genotype.

*Rosa* 'RUIZ012A' exhibits a compact habit.

*Rosa* 'RUIZ012A' exhibits red flowers.

*Rosa* 'RUIZ012A' exhibits a long plant life.

BRIEF DESCRIPTION OF THE DRAWING

The accompanying drawing illustrates the distinguishing traits of *Rosa* 'RUIZ012A'. The plant in the drawing is 12 weeks old and was glass greenhouse grown in a 10 cm. container. The drawing shows the overall plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Rosa* cultivar named 'RUIZ012A'. Data was collected in Amstelveen, The Netherlands from 12 weeks old glass greenhouse grown plants in a 10 cm. container. The time of year was March and the average temperature was 18° Centigrade during the day and 16° Centigrade at night. The light level was 5000 Lux. No photoperiodic treatments were used. Bonsi growth retardant was applied. Color determinations are in accordance with The Royal Horticultural Society Colour Chart 1995 except where general color terms of ordinary dictionary significance are used. The growing requirements are similar to the species.

Botanical classification: *Rosa* 'RUIZ012A'.
Type: Perennial.
Use: Ornamental.
Parentage: 'RUIZ012A' is a hybrid plant that resulted from the induced hybridization of the following parent plants:
*Female parent.*—*Rosa* 'Ruiscar' (not patented).
*Male parent.*—*Rosa* 'Poulracos' (not patented).
Vigor: Moderate.
Growth rate: Approximately 8 cm. per month.

Growth habit: Compact.
Plant shape: Flattened globose.
Suitable container size: 10 cm. diameter container.
Height: Average 20–25 cm. in height.
Width: Average 25–30 cm. in width.
Hardiness: Low temperature tolerance is 0 degrees Centigrade, high temperature tolerance is 45 degrees Centigrade.
Propagation: Softwood cuttings.
Time to initiate roots: Approximately 14 days are required to produce roots on an initial cutting.
Crop time: Approximately 10 weeks are required to achieve a finished plant from a rooted cutting.
Root system: Fine and fibrous.
Stem:
*Branching habit.*—Free branching.
*Pinching.*—Yes.
*Average number of lateral branches.*—8.
*Stem diameter.*—Approximately 0.5 cm. in diameter.
*Stem length.*—Approximately 17 cm. in length.
*Stem strength.*—Moderate.
*Stem color.*—144A.
*Pubescence.*—Absent.
*Internode length.*—Approximately 1.5 cm. between nodes.
*Shape.*—Round.
*Surface.*—Glabrous, slightly glossy.
Foliage:
*Durability to foliage stresses.*—Moderate.
*Texture.*—Smooth and glossy.
*Leaf arrangement.*—Imparipinnate.
*Compound or single.*—Compound.
*Quantity of leaves per lateral branch.*—Approximately 8.
*Quantity of leaflets per leaf.*—3, 5 or 7.
*Leaf margin.*—Serrate, 6 teeth per cm.
*Pubescence.*—Absent.
*Leaflet shape.*—Elliptic.
*Leaflet apex.*—Acute.
*Leaflet base.*—Rounded.
*Leaflet length.*—2.7 cm. in length.
*Leaflet width.*—1.8 cm. in width.
*Young leaf color* (*upper surface*).—137A.
*Young leaf color* (*under surface*).—191B.
*Mature leaf color* (*upper surface*).—139A.
*Mature leaf color* (*under surface*).—191A.
*Vein pattern.*—Pinnate.
*Vein color* (*upper surface*).—145C.
*Vein color* (*under surface*).—147D.
*Leaf attachment.*—Petiolate.
*Petiole dimensions.*—1.5 cm. in length and 1.2 mm. in width, for terminal leaflet 5 cm in length.
*Petiole color.*—Upper side 147B, under side 146D.
*Stipules.*—Present.
*Stipule dimensions.*—7 mm. in length and 5 mm. in width.
*Stipule color.*—145B.
*Prickles.*—1–2 prickles present on under side of petiole, color 150D.
*Auricles.*—Present.
*Auricle dimensions.*—3 mm. in length and 1 mm. in width.
*Auricle color.*—147B.
Flower:
*Flower arrangement.*—Flowers borne on single peduncles with 3 or 4 flowers per spray.
*Flower type.*—Semi-double.
*Flowering habit.*—Continuous.
*Quantity of flowers per lateral stem.*—Approximately 4.
*Quantity of flower bud per lateral stem.*—Approximately 4.
*Quantity of flowers and buds per plant.*—Approximately 20.
*Flowering season.*—Late spring to autumn outdoors, continuous under greenhouse conditions.
*Fragrance.*—None.
*Flower bud length.*—1.5 cm. in length.
*Flower bud diameter.*—1 cm. in diameter.
*Flower bud shape.*—Ovate.
*Bud color.*—138A.
*Rate of bud opening.*—1 week.
*Flower aspect.*—Upright.
*Flower shape.*—Rounded, semi-double.
*Flower dimensions.*—4 cm. in diameter and 1.25 cm. in height.
*Flower longevity.*—Lasts approximately 12–14 days on plant.
*Petal color when opening* (*under side*).—45D.
*Petal color when opening* (*upper side*).—45A.
*Petal color fully opened* (*upper side*).—45A.
*Petal color fully opened* (*under side*).—45D.
*Petal appearance.*—Dull.
*Petal texture.*—Velvety.
*Number of petals.*—30.
*Petals fused or unfused.*—Unfused.
*Petal shape.*—Broad obovate.
*Petal margin.*—Entire.
*Petal apex.*—Obtuse.
*Petal base.*—Rounded.
*Petal dimensions.*—2 cm. in length and 2 cm. in width.
*Petal color fading to.*—Not fading.
*Petaloids.*—Absent.
*Self-cleaning or persistent.*—Persistant.
*Peduncle strength.*—Strong.
*Peduncle color.*—137A.
*Peduncle dimensions.*—1 cm. in length and 2 mm. in diameter.
*Peduncle angle.*—0°.
*Pedicels.*—Present.
*Pedicel dimensions.*—1.5 to 2 cm. in length and 2 mm. in diameter.
*Pedicel angle.*—Average 45°.
*Pedicel color.*—137C.
*Sepal color* (*upper side*).—138B.
*Sepal color* (*under side*).—138B.
*Sepal arrangement.*—Rotate.
*Number of sepals.*—5.
*Sepal shape.*—Ensiform.
*Sepal margin.*—Celiate.
*Sepal apex.*—Caudate.
*Sepal base.*—Rounded.
*Sepal dimensions.*—1.7 cm. in length and 6 mm. in width.
*Petaloids.*—Absent.
*Calyx shape.*—Rotate.
*Calyx dimensions.*—5 mm. in length and 4 mm. in diameter.
Reproduction organs:
*Stamen number.*—Approximately 65.
*Anther shape.*—Bilobate.

*Anther dimensions.*—1.3 mm. in diameter and 2.5 mm. in length.
*Anther color.*—22B.
*Amount of pollen.*—Low.
*Pollen color.*—174B.
*Pistil number.*—26 in number.
*Pistil dimensions.*—5 mm. in length and 1.5 mm. in diameter.
*Stigma shape.*—Campanulate.
*Stigma color.*—159B.
*Style dimensions.*—7 mm. in length.
*Style color.*—159D.
*Ovary color.*—159D.

Seed: Seed production has not been observed.
Disease resistance: Not resistant to powdery mildew.
Pest resistance: Has not been observed.

It is claimed:

1. A new and distinct variety of *Rosa* plant named 'RUIZ012A' as described and illustrated.

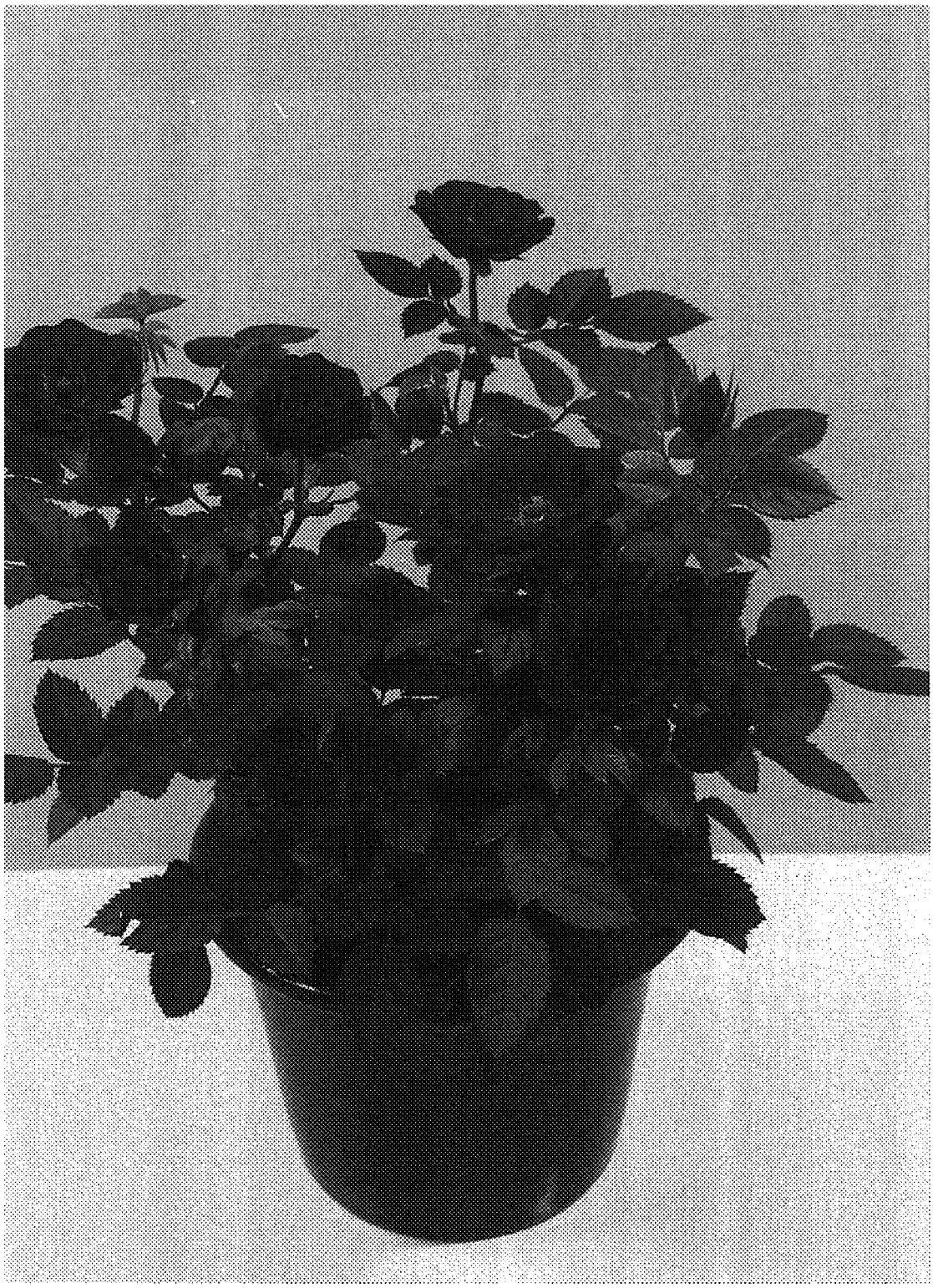

* * * * *